United States Patent
Oda

(10) Patent No.: US 6,679,940 B1
(45) Date of Patent: Jan. 20, 2004

(54) AIR CLEANER AND ITS IONIZING UNIT

(75) Inventor: Yasuhiro Oda, Sakai (JP)

(73) Assignee: Daikin Industres, Ltd., Osaka (JP)

( * ) Notice: Subject to any disclaimer, the term of this patent is extended or adjusted under 35 U.S.C. 154(b) by 0 days.

(21) Appl. No.: 10/070,946

(22) PCT Filed: Aug. 30, 2000

(86) PCT No.: PCT/JP00/05894

§ 371 (c)(1),
(2), (4) Date: Mar. 13, 2002

(87) PCT Pub. No.: WO01/19419

PCT Pub. Date: Mar. 22, 2001

(30) Foreign Application Priority Data

Sep. 14, 1999 (JP) .............................. 11-260720

(51) Int. Cl.[7] .............................. B03C 3/011
(52) U.S. Cl. ................. 96/55; 96/58; 96/77; 96/94; 96/96
(58) Field of Search ............. 96/16, 55, 57–59, 96/77, 94, 96, 98

(56) References Cited

U.S. PATENT DOCUMENTS

| | | | | |
|---|---|---|---|---|
| 2,447,933 A | | 8/1948 | Cummings ................. 96/84 |
| 3,438,180 A | * | 4/1969 | Klouda ..................... 96/58 |
| 3,626,668 A | * | 12/1971 | Cardiff ..................... 96/58 |
| 3,735,560 A | * | 5/1973 | Wellman ................... 96/62 |
| 3,783,588 A | * | 1/1974 | Hudis ....................... 96/58 |
| 3,985,524 A | * | 10/1976 | Masuda .................... 96/32 |
| 4,007,024 A | | 2/1977 | Sallee et al. ............... 96/65 |
| 4,354,858 A | * | 10/1982 | Kumar et al. .............. 95/78 |
| 4,405,342 A | * | 9/1983 | Bergman ................... 95/69 |
| 4,516,991 A | | 5/1985 | Kawashima ............... 96/55 |
| 4,549,887 A | * | 10/1985 | Joannou .................... 96/58 |
| 5,092,396 A | * | 3/1992 | Murano et al. ............ 165/119 |
| 5,290,343 A | * | 3/1994 | Morita et al. .............. 96/39 |
| 5,573,577 A | * | 11/1996 | Joannou .................... 96/66 |
| 5,622,543 A | | 4/1997 | Yang ........................ 96/58 |
| 6,149,717 A | * | 11/2000 | Satyapal et al. ............ 96/16 |
| 6,156,104 A | * | 12/2000 | Jeong ........................ 96/88 |

FOREIGN PATENT DOCUMENTS

| | | | |
|---|---|---|---|
| GB | 745609 | 2/1956 | |
| JP | 62-101257 | 5/1987 | |
| JP | 1-128844 | 9/1989 | |
| JP | 4-70148 | 6/1992 | |
| JP | 05-023615 | 2/1993 | |
| JP | 6-47313 | * 2/1994 | ............. 96/96 |
| JP | 08-173843 | 7/1996 | |
| JP | 8-173843 | 7/1996 | |
| JP | 10-309402 | 11/1998 | |
| JP | 11-114046 | 4/1999 | |
| JP | 11-114444 | 4/1999 | |
| JP | 11-128769 | 5/1999 | |
| WO | WO99/19052 | 4/1999 | |
| WO | WO99/19072 | 4/1999 | |

* cited by examiner

Primary Examiner—Richard L. Chiesa
(74) Attorney, Agent, or Firm—Rabin & Berdo, P.C.

(57) ABSTRACT

When an ionization section is taken out of a main body housing of a conventional air cleaner in order to wash the ionization section, an ionization line may be cut by being accidentally touched. In order to avoid this problem, a pre-filter (7) is mounted on a front surface of an ionization and dust collection unit (6) so as to be detachable. The pre-filter (7) is slidably guided by guide furrings (23) in a sub-frame (12), and is mounted on a front surface of the sub-frame (12). When the pre-filter (7) is mounted, ionization lines (15) are not exposed, so that the pre-filter (7) protects the ionization lines (15). When the ionization and dust collection unit (6) is detached from the main body housing, therefore, there is no problem that the ionization lines (15) might be cut by being accidentally touched with worker's hands, for example.

8 Claims, 4 Drawing Sheets

AIR CLEANER AND ITS IONIZING UNIT

DESCRIPTION OF THE INVENTION

The present invention relates to an air cleaner, and more particularly, to an air cleaner adapted to charge dust particles suspended in air using an ion shower and to capture the charged dust particles using the principle of electrostatic adsorption. Further, it relates to an ionizing unit for such an air cleaner.

DESCRIPTION OF THE PRIOR ART

Air cleaners of an electric dust collection type for charging dust particles included in air and capturing the charged dust particles by electrostatic adsorption have been known. Such an air cleaner comprises an ionization section (a discharge section) for charging the dust particles. The ionization section comprises an ionization line and an opposite electrode which serve as discharge electrodes, and the dust particles included in air passing between the ionization line and the opposite electrode are charged using an ion shower produced by discharging the ionization line.

The charged dust particles are captured by being electrostatically adsorbed in the dust collection section.

In the air cleaner of an electric dust collection type, the ionization section and the dust collection section must be periodically cleaned, and a filter in the dust collection section must be replaced in order to keep the dust collection performance good.

The ionization section and the dust collection section are generally formed as an ionizing unit for convenience of washing or the like so that they are detachable from a main body housing. When the ionizing unit is taken out by opening the main body housing, the ionization line in the ionizing unit is exposed, so that it may be erroneously cut or damaged. The reason for this is that the ionization line is difficult to see because it is a very thin metal line, so that it can easily be touched erroneously by a worker's hands or by other parts.

SUMMARY OF THE INVENTION

The present invention has been made in order to solve such a problem and has for its object to provide an air cleaner having a protective structure for protecting an ionization line provided in an ionization section. Further, an object of the present invention is to provide an air cleaner and an ionizing unit which are so improved that an ionization line is not erroneously cut when an ionization section (an ionizing unit) is taken out.

In accordance with one aspect of the invention, an air cleaner of the type that includes a pre-filter for capturing relatively large dirt and dust in air; an ionization section having an ionization line and an opposite electrode for charging dust particles in air; and a dust collection section for capturing the charged dust particles, is characterized in that the pre-filter is mounted on the ionization section so as to be detachable.

Even when the main body housing is opened to take out the ionization section, the pre-filter is mounted on the ionization section so that the ionization line is protected by the pre-filter. That is, the ionization line is not exposed, so that a worker cannot accidentally touch the ionization line. When the ionization section is washed, the pre-filter may be detached from the ionization section which has been detached from the main body housing. The ionization line is exposed by detaching the pre-filter. In this case, however, the worker performs work while paying attention to the ionization line, so that the ionization line may not be erroneously cut.

The ionization section and the dust collection section may be integrated as one unit, and the pre-filter may be mounted on a front surface side of an ionization and dust collection unit thus integrated so as to be detachable. Accordingly, the unit can be simply detached and mounted. Moreover, when the unit is taken out or mounted, the ionization line in the unit is protected by the pre-filter. Accordingly, the ionization line is not directly touched with worker's hands, for example, and is not erroneously cut.

The ionization and dust collection unit may have a main frame and a sub-frame, the sub-frame being made attachable and detachable to and from the main frame on the side of a front surface of the main frame, with the ionization line being stretched over the sub-frame and the detachable pre-filter being mounted on a front surface of the sub-frame. The main frame may be provided with the opposite electrode, and support a filter for capturing the charged dust particles in the air by electrostatic adsorption.

Such an arrangement makes washing the unit easy. That is, the integrated unit may be taken out of the main body housing, and is also easy to mount.

On the other hand, the unit obtained by the integration which has been detached from the main body housing can be decomposed into the main frame and the sub-frame. The ionization line which is protected by the pre-filter is stretched over the sub-frame, and the opposite electrode is provided in the main frame. Accordingly, it is possible to detach the pre-filter from the sub-frame and carefully wash the ionization line. The opposite electrode in the main frame is, in many cases, very dirty, but it is possible to wash it without paying attention to the ionization line.

The main frame may have a roll filter accommodation section provided at its one end, and a rear surface of the main frame may support the periphery of the film-shaped filter corresponding to one time of use which is pulled out of a roll filter accommodated in the roll filter accommodation section.

Such an arrangement makes the air cleaner convenient for handling.

According to a second aspect of the invention, an ionizing unit for an air cleaner for charging dust particles included in the air and capturing the charged dust particles, is characterized by comprising a frame and an ionization line which is stretched over the frame; an opposite electrode provided in the frame so as to be opposite to the ionization line in a predetermined state; and a pre-filter mounted on a front surface of the frame so as to be detachable.

A dust collection section for capturing the charged dust particles may be mounted on the frame, with the dust collection section including a filter arranged such that the periphery thereof is supported on a rear surface of the frame for capturing the charged dust particles in the air by electrostatic adsorption.

The frame may have an accommodation section which can accommodate a roll filter which is a film-shaped filter having such a length that it can be used a plurality of times wound in a roll shape provided at its one end.

Since the pre-filter is mounted on the front surface of the frame so as to be detachable, in accordance with the second aspect of the invention, the ionization line in the ionizing unit is protected by the pre-filter. That is, the ionization line is covered with the pre-filter, and is not exposed. Accordingly, the ionization line is not prone to be accidentally touched with a worker's hands, for example, and may not be erroneously cut.

At the time of washing, it is possible to pay careful attention to the ionization line by detaching the pre-filter to expose the ionization line. Further, the pre-filter can independently be washed when detached.

The frame may have a main frame and a sub-frame, the sub-frame being constructed so as to be attachable and detachable to and from the main frame on the side of its front surface. The ionization line and the pre-filter may be provided in the sub-frame, and the opposite electrode and the dust collection section may be provided in the main frame.

With such a construction, the ionization line and the opposite electrode are easier to wash. Further, when they are integrated by being combined, the air cleaner has a structure easy to handle in which the ionization line is protected by the pre-filter.

As described in the foregoing, according to the present invention, it is possible to provide an air cleaner having a superior structure in which the ionization line is protected by the pre-filter so that it may not be cut.

DESCRIPTION OF THE PREFERRED EMBODIMENT

Figure 1:
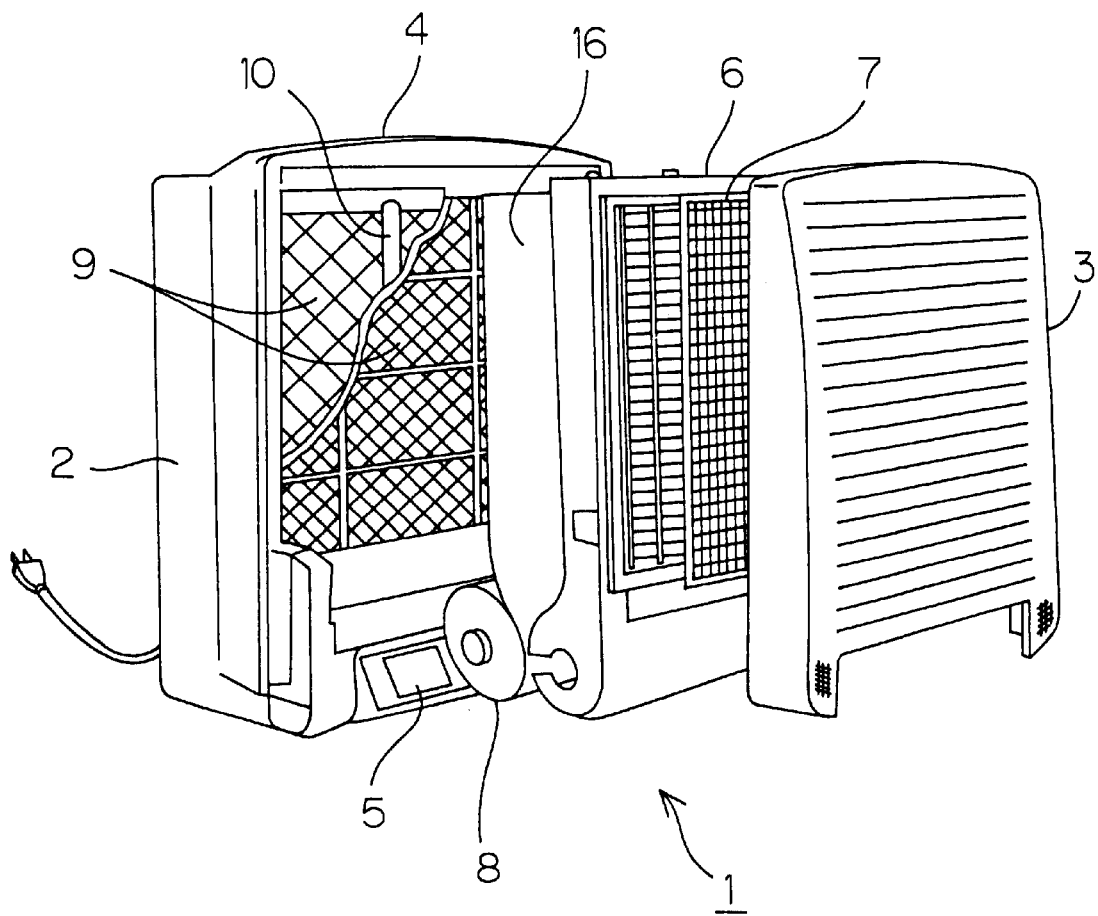
FIG. 1 is an exploded perspective view showing the overall construction of an air cleaner 1 according to an embodiment of the present invention.

An embodiment of the present invention will be specifically described while referring to the drawings.

FIG. 1 is an exploded perspective view showing the overall construction of an air cleaner 1 according to an embodiment of the present invention.

The air cleaner 1 has a main body housing 2 and a front panel 3 which is fitted to a front surface of the main body housing 2. A motor (not shown) and a blast fan which is rotated by the motor are provided in the main body housing 2. Air is drawn from the front panel 3 by the blast fan, is cleaned, and is then blown off from a blow-off grill 4 on an upper surface of the main body housing 2. A display and operation section 5 is provided at a lower part of the front surface of the main body housing 2. The display and operation section 5 comprises an operation section for turning a power supply in the air cleaner 1 on/off and switching an operation mode and a display section for displaying an operating state.

The main body housing 2 accommodates an ionization and dust collection unit 6. The ionization and dust collection unit 6 has a pre-filter 7 attached to its front surface. The pre-filter 7 is for capturing relatively large dirt and dust. In the ionization and dust collection unit 6, an ionization line and an opposite electrode for charging dust particles included in air passing through the unit, described later, are incorporated. A film-shaped filter 16 for capturing the charged dust particles is mounted on a rear surface of the ionization and dust collection unit 6. The film-shaped filter 16 is pulled out of a roll filter 8.

The main body housing 2 further comprises two layers of photocatalyst elements 9 arranged on the front and rear sides and an inverter lamp 10 arranged therebetween in an inner part of the ionization and dust collection unit 6. Each photocatalyst element 9 is a thin plate-shaped member having a honey-comb structure which passes air drawn from its front surface backward, and supports a photocatalyst such as titanium oxide. The inverter lamp 10 directs light to the photocatalyst elements 9, to activate the photocatalyst carried in the elements. An odorous constituent in air can be removed by activating the photocatalyst elements. Further, the inverter lamp 10 has antibacterial and antiviral effects.

Figure 2:
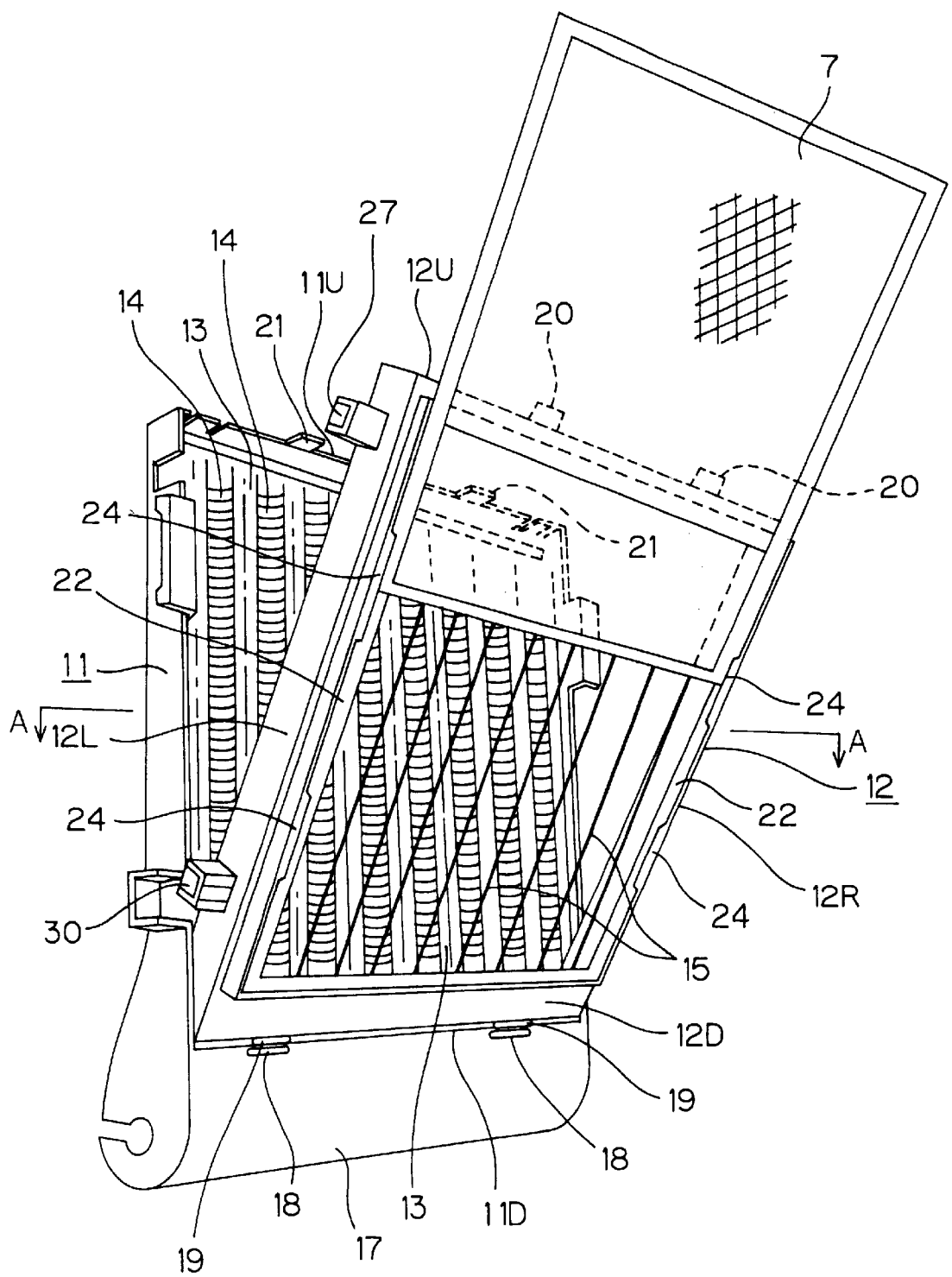
FIG. 2 is a perspective view of an ionization and dust collection unit according to the embodiment of the present invention.

FIG. 2 is a perspective view of the ionization and dust collection unit 6. The ionization and dust collection unit 6 has a main frame 11 and a sub-frame 12.

The main frame 11 is formed of an insulating material such as resin, and an opening enclosed by the frame comprises an opposite electrode group. The opposite electrode group has nine opposite electrodes 13, arranged parallel to one another, extending in the vertical direction in the present embodiment. Each of the opposite electrodes 13 has a U shape in cross section, and the adjacent opposite electrodes 13 connect with one another by a lot of thin connecting pieces 14 curved in a concave shape. That is, the nine opposite electrodes 13 are formed by sheet metal forming from one metal plate. The adjacent opposite electrodes 13 connect with each other by the thin connecting pieces 14 in order that air passes therebetween.

The sub-frame 12 is also formed of an insulating material such as resin. Eight ionization lines 15 extending in the vertical direction are stretched parallel to one another in an opening enclosed by the frame.

The sub-frame 12 is constructed so as to be attachable and detachable to and from the main frame 11. When the sub-frame 12 is fitted in the main frame 11, the ionization lines 15 are arranged between the opposite electrodes 13 to be extended parallel to the opposite electrodes 13. That is, the eight ionization lines 15 and the nine opposite electrodes 13 are parallel and alternately opposite to one another.

Furthermore, the ionization lines 15 can be separated from the opposite electrodes 13 by detaching the sub-frame 12 from the main frame 11.

When the ionization lines 15 and the opposite electrodes 13 are made separable, the ionization lines 15 and the opposite electrodes 13 are easily maintained and specifically, are easy to wash. That is, dirt adheres to the ionization lines 15 and the opposite electrodes 13 as the air cleaner is used. Accordingly, the ionization lines 15 and the opposite electrodes 13 must be periodically washed. If an integrated construction where the ionization lines 15 and the opposite electrodes 13 could not be separated from each other were used, there would be some problems. For example, the thin ionization lines 15 might be cut at the time of washing unless special attention is paid. Further, the opposite electrodes 13 and the connecting plates 14 would be hard to wash because the ionization lines 15 would interfere.

In the present embodiment, the ionization lines 15 and the opposite electrodes 13 can be separately washed or cleaned by separating them. Consequently, the ionization lines 15 are not in danger of being cut at the time of washing the opposite electrodes 13. Further, the opposite electrodes 13 can be elaborately washed without paying attention to the ionization lines 15.

A roll filter accommodation section 17 is integrally formed at a lower end of the main frame 11. The roll filter accommodation section 17 accommodates the roll filter 8, which is a film-shaped filter having such a length that it can be used a plurality of times and which is wound in a roll shape, as shown in FIG. 1. The film-shaped filter 16, corresponding to use of the roll filter 8 one time, is pulled off the roll filter 8 and supported on a rear surface of the main frame 11. The film-shaped filter 16 is a filter for electrostatic adsorption, which captures charged dust particles by electrostatic adsorption using an ion shower produced by the ionization lines 15.

When the opposite electrodes 13 are washed, the roll filter 8 and the film-shaped filter 16 which has been pulled out are detached from the main frame 11.

The sub-frame 12 is fitted in the main frame 11 in the following manner. Two engagement holes 18 are formed on the right and left sides in a lower frame 11D of the main frame 11 (an upper surface of the roll filter accommodation section 17). Two projections 19 which are respectively engaged with the engagement holes 18 are provided in a lower frame 12D of the sub-frame 12. The projections 19 are fitted in the engagement holes 18, and an upper frame 12U of the sub-frame 12 is rotated toward the far side (backward), centered around the lower frame 12D, thereby making it possible to fit the sub-frame 12 in the main frame 11. Two locking members 20 are provided in a protruding manner upward on the right and left sides in the upper frame 12U of the sub-frame 12. On the other hand, two locking members 21 are also provided in a protruding manner forward in an upper frame 11U of the main frame 11.

Figure 3A:
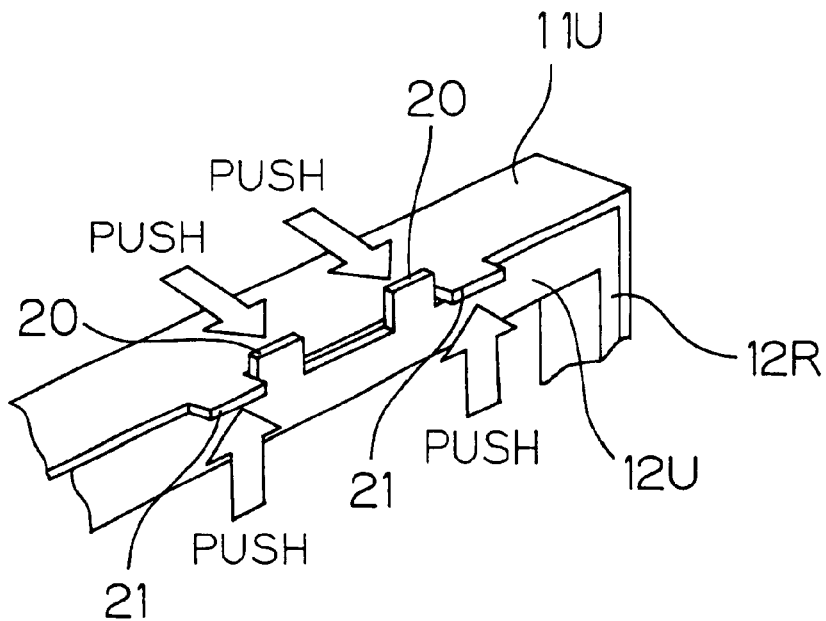
FIG. 3 is a diagram for explaining a locking structure in which a sub-frame 12 is fitted in a main frame 11, to fix a fitted state in the embodiment of the present invention.
Figure 3B:
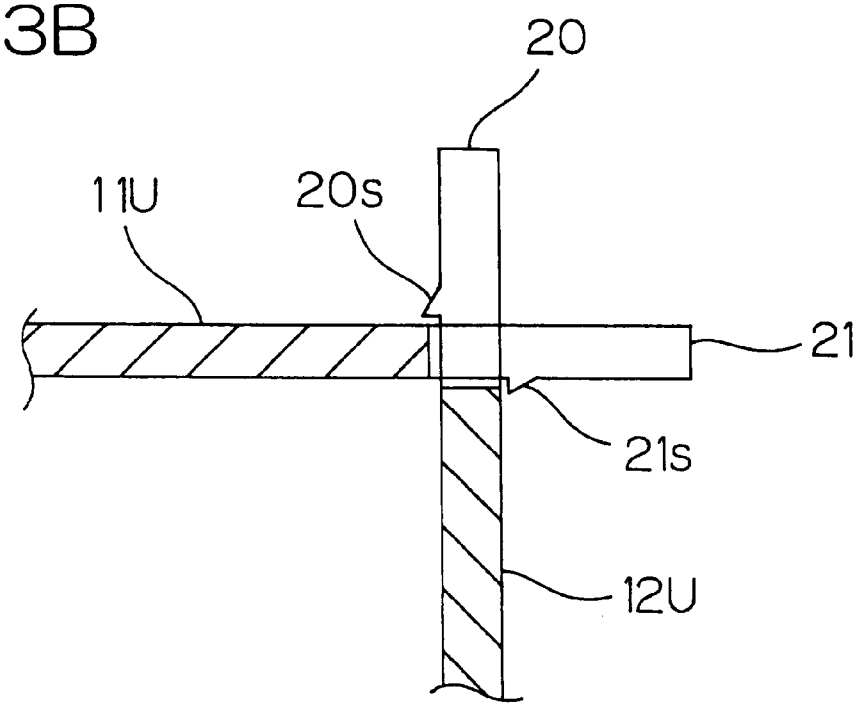

In a state where the sub-frame 12 is fitted in the main frame 11, as shown in FIG. 3A, the two locking members 20 provided in the upper frame 12U of the sub-frame 12 and the two locking members 21 provided in the upper frame 11U of the main frame 11 are in a state where they are adjacent to each other in orthogonal directions. The locking members 20 and 21 are respectively provided with small steps 20s and 21s, as shown in FIG. 3B. The steps 20s and 21s respectively lock the upper frame 11U of the main frame 11 and the upper frame 12U of the sub-frame 12. Accordingly, the sub-frame 12 can be held to the main frame 11.

When the sub-frame 12 is detached from the main frame 11, a force may be applied such that the locking members 20 and 21 are respectively pressed in opposite directions to the steps 20s and 21s to rotate the upper frame 12U of the sub-frame 12 toward this side (forward), as shown in FIG. 3A.

In the present embodiment, the pre-filter 7 is mounted on the front surface of the sub-frame 12. Specifically, referring to FIG. 2, each of a right frame 12R and a left frame 12L of the sub-frame 12 has a guide furring 23 for sliding the pre-filter 7 upward and downward formed on its front surface. The guide furring 23 comprises a hook 24 having an L shape in cross section. Both the sides of pre-filter 7 which are slid along the guide furrings 23 are respectively prevented from coming off the guide furrings 23 by the hooks 24. Consequently, the pre-filter 7 can be mounted on the front surface of the sub-frame 12 by sliding the pre-filter 7 downward from the top of the sub-frame 12.

Figure 4:
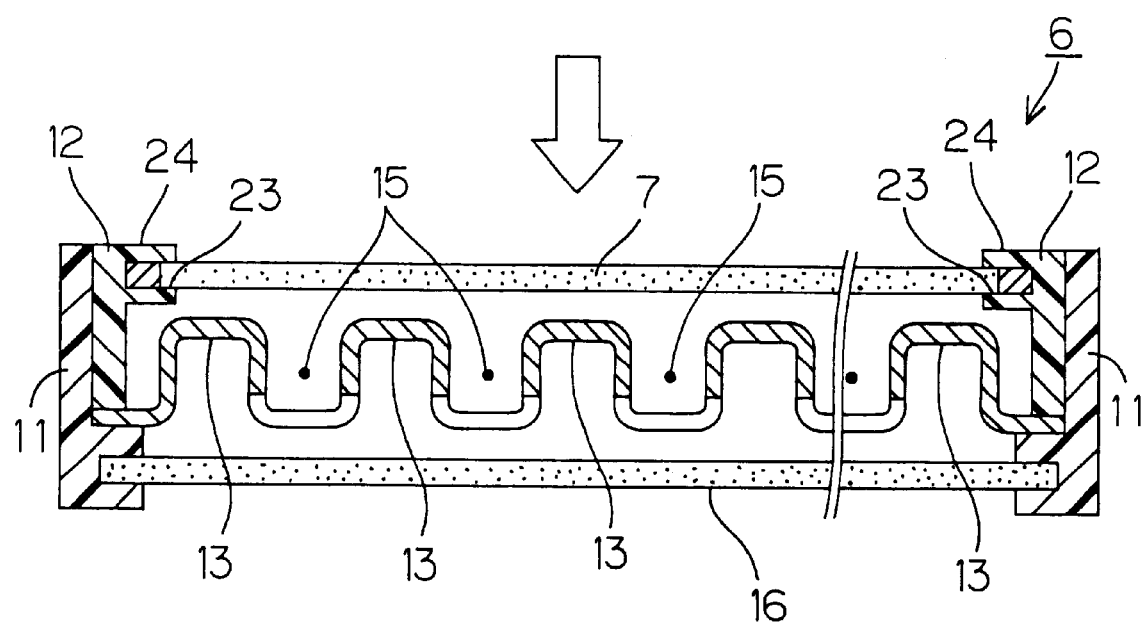
FIG. 4 is a perspective view taken along a line A—A shown in FIG. 2 and a cross-sectional end elevation in a state where an ionization and dust collection unit 6 according to the embodiment of the present invention is assembled.

FIG. 4 is a perspective view taken along a line A—A and is a cross-sectional end elevation in a state where the ionization and dust collection unit 6 is assembled. A hollow arrow in FIG. 4 indicates the flow of air.

When the pre-filter 7 is mounted on the front surface of the sub-frame 12, the pre-filter 7 protects the ionization lines 15. The ionization lines 15 are difficult to see because they are significantly thin lines. Accordingly, the ionization lines 15 may be touched with a worker's hands in cases such as a case where the ionization and dust collection unit 6 is detached from the main body housing 2, which is not desirable because the worker may hurt his hands or cut an ionization line 15. Conventionally, the pre-filter 7 is attached to a rear surface of the front panel 3 (see FIG. 1). When the front panel 3 is detached, therefore, the front surface of the ionization and dust collection unit 6 appears so that the ionization lines 15 are exposed. If the ionization and dust collection unit 6 is detached, therefore, there are some problems. For example, the ionization lines 15 may be cut without being noticed.

In the present embodiment, the pre-filter 7 is mounted on the sub-frame 12 and the pre-filter 7 protects the ionization lines 15, as shown in FIG. 4. When the ionization and dust collection unit 6 is detached from the main body housing 2, therefore, the ionization lines 15, which are protected by the pre-filter 7, are not susceptible to being accidentally cut, for example.

In the above-mentioned embodiment, description was made of an example in which the ionization and dust collection unit 6 is integrated, and the frame is constituted by the main frame 11 and the sub-frame 12. However, the present invention may be directed to an air cleaner in which an ionization section and a dust collection section are separately provided, in which a pre-filter is mounted on a front surface of the ionization section so as to be detachable.

The present invention may be so constructed that an ionization section is constituted by a single frame which cannot be separated into a main frame and a sub-frame, and the single frame comprises an ionization line and an opposite electrode. Further, the present invention may be so constructed that a dust collection unit is incorporated into such an ionization section.

In short, the present invention is directed to an air cleaner comprising an ionization section so constructed that an ionization line is protected by mounting a pre-filter, and an ionizing unit for the air cleaner.

Although a construction such that the pre-filter 7 is attached and detached to and from the front surface of the sub-frame 12 by being slid has been described, the present invention may be directed to such constructions that the pre-filter 7 is screwed, for example, to the front surface of the sub-frame 12, attached thereto on the side of its front surface by a hook or the like, or attached thereto by another mounting method.

The present invention is not limited to the above-mentioned embodiment, and various modifications are possible within the range of the claims.

This application claims priority benefits under the convention on the basis of Japanese Patent Application NO. 11-260720 filed with the Japanese Patent Office on Sep. 14, 1999, the disclosure of which is incorporated herein by reference.

What is claim is:

1. An ionizing unit for an air cleaner for charging dust particles included in air and capturing the charged dust particles, comprising:
   a main frame (11);
   a sub-frame (12) detachably mounted on the main frame (11), the sub-flame (12) having a front side;

an ionization line (15) which is mounted on the sub-frame (12);

an opposite electrode (13) mounted on the main frame (11) so as to be opposite to the ionization line (15) when the sub-frame (12) is mounted on the main frame (11); and a pre-filter (7) mounted on a front side of the sub-frame (12) so as to be detachable.

2. The ionizing unit for the air cleaner according to claim 1, further comprising:

a filter (16) having a peripheral portion that is supported on a rear surface of the main frame (11) for capturing charged dust particles in the air by electrostatic adsorption.

3. The ionizing unit for the air cleaner according to claim 2, wherein the filter (16) is a section of a roll filter (8), and the main frame 11 has an accommodation section (17) which can accommodate the roll filter (8).

4. The ionizing unit for the air cleaner according to claim 1, wherein the main frame (11) has an accommodation section (17) which can accommodate a roll filter (8), from which a section can be pulled and supported at a rear side of the main frame (11).

5. The air cleaner according to claim 1, further comprising at least one additional ionization line (15) mounted on the sub-frame (12), and at least one additional opposite electrode (13) mounted on the main frame (11).

6. An air cleaner, comprising:

an integrated ionization and dust collection unit (6) that includes a main frame (11) having a front side, a sub-frame (12) that is detachably mounted on the front side of the main frame (11), the sub-frame (12) having a front side, an ionization line (15) mounted on the sub-frame (12), an opposite electrode (13) mounted on the main frame (11), the opposite electrode (11) cooperating with the ionization line (15) to charge dust particles in air passing through the air cleaner, and a filter (16) supported on the main frame (11) to capture the charged dust particles; and a pre-filter (7) for capturing relatively large dirt and dust in the air, the pre-filter (7) being detachably mounted on the front side of the sub-frame (12).

7. The air cleaner according to claim 6, further comprising at least one additional ionization line (15) mounted on the sub-frame (12), and at least one additional opposite electrode (13) mounted on the main frame (11).

8. The air cleaner according to claim 6, wherein the filter (16) is a section of a roll filter (8), and the main frame (11) has a roll filter accommodation section (17) provided at one end thereof to accommodate the roll filter (8), and a rear side of the main frame (11) supports a periphery of the section of the roll filter (8), which is pulled out from the roll filter (8) for one-time use.

* * * * *